United States Patent
An et al.

(10) Patent No.: US 9,579,058 B2
(45) Date of Patent: Feb. 28, 2017

(54) SENSOR GUIDED RESPONSE TO ANTI-ARRHYTHMIC CHANGES

(71) Applicant: Cardiac Pacemakers, Inc., St. Paul, MN (US)

(72) Inventors: Qi An, Blaine, MN (US); Pramodsingh Hirasingh Thakur, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 14/831,376

(22) Filed: Aug. 20, 2015

(65) Prior Publication Data
US 2016/0081619 A1 Mar. 24, 2016

Related U.S. Application Data

(60) Provisional application No. 62/053,950, filed on Sep. 23, 2014.

(51) Int. Cl.
| | |
|---|---|
| *A61B 5/04* | (2006.01) |
| *A61B 5/00* | (2006.01) |
| *A61B 7/04* | (2006.01) |
| *A61B 5/0245* | (2006.01) |
| *A61B 5/0452* | (2006.01) |
| *A61B 7/00* | (2006.01) |

(52) U.S. Cl.
CPC .......... *A61B 5/4848* (2013.01); *A61B 5/0245* (2013.01); *A61B 5/04012* (2013.01); *A61B 5/0452* (2013.01); *A61B 5/7235* (2013.01); *A61B 5/746* (2013.01); *A61B 7/00* (2013.01); *A61B 7/04* (2013.01)

(58) Field of Classification Search
CPC . A61B 5/4848; A61B 5/0245; A61B 5/04012; A61B 5/0452; A61B 5/746
See application file for complete search history.

(56) References Cited

U.S. PATENT DOCUMENTS

| | | | | |
|---|---|---|---|---|
| 2002/0128563 A1* | 9/2002 | Carlson | ................ | A61N 1/3622 600/509 |
| 2013/0268012 A1* | 10/2013 | Sison | ................ | A61N 1/36578 607/4 |

OTHER PUBLICATIONS

Boudoulas, H., et al., "Linear Relationship Between Electrical Systole, Mechanical Systole, and Heart Rate", Chest, 80: 5, (Nov. 1981), 613-617.

Waggoner, Alan D., et al., "Improvements in Left Ventricular Diastolic Function After Cardiac Resynchronization Therapy Are Coupled to Response in Systolic Performance", Journal of the American College of Cardiology, vol. 46, No. 12, (2005), 2244-2249.

* cited by examiner

*Primary Examiner* — Robert N Wieland
(74) *Attorney, Agent, or Firm* — Schwegman Lundberg & Woessner, P.A.

(57) ABSTRACT

A patient's response to anti-arrhythmic drug changes can be monitored using cardiac activity information, such as using cardiac electromechanical time intervals adjusted for heart rate. A cardiac electromechanical time interval can include an R-S2 interval or an S2-R interval. Tracking changes in cardiac electromechanical time intervals adjusted for heart rate can be used to provide information about a patient, including anti-arrhythmic drug effect information and patient condition information.

20 Claims, 7 Drawing Sheets

SENSOR GUIDED RESPONSE TO ANTI-ARRHYTHMIC CHANGES

CLAIM OF PRIORITY

This application claims the benefit of priority under 35 U.S.C. §119(e) of U.S. Provisional Patent Application Ser. No. 62/053,950, filed on Sep. 23, 2014, which is herein incorporated by reference in its entirety.

BACKGROUND

Anti-arrhythmic drugs (also referred to as "anti-arrhythmic agents" or "antiarrhythmic drugs") are a group of pharmaceuticals that may be used to suppress abnormal heart rhythms (also referred to as "cardiac arrhythmias"). Examples of types of cardiac arrhythmias may include ventricular or supraventricular arrhythmias, such as non-sustained ventricular tachycardia, sustained ventricular tachycardia, ventricular fibrillation, premature ventricular contractions, long Q-T syndrome, atrial fibrillation, atrial flutter, and premature atrial contractions.

Anti-arrhythmic drugs may be classified, such as based on exerting inhibitory activity on different phases of the cardiac action potential. Anti-arrhythmic drugs may include Class III anti-arrhythmic drugs (also referred to as "Type III"). The mechanism of action of Class III anti-arrhythmic drugs may include inhibiting potassium channel outflow, which may increase the refractory period of the cardiac action potential.

An electrocardiogram (EKG or ECG) represents an intrinsic electrical cardiac signal, which includes atrial and ventricular depolarizations. Class III anti-arrhythmic drugs may prolong the Q-T interval of the EKG. Class ill anti-arrhythmic drugs may have other effects, such as slowing heart rate, slowing atrioventricular nodal conduction, and prolonging refractoriness. Examples of Class III anti-arrhythmic drugs may include amiodarone and dofetilide. Amiodarone may have other effects, and thus may be included in Classes I, II, and IV. Because amiodarone may prolong the Q-T interval, it may be considered pro-arrhythmic.

Patients with cardiac arrhythmias may be treated using anti-arrhythmic drugs, medical devices, other therapies, or any combination thereof. Medical devices may be ambulatory or non-ambulatory. Ambulatory medical devices (AMDs) may be used to monitor and/or treat patients with cardiac conditions. Examples of AMDs may include subcutaneous and other implantable medical devices (IMDs), wearable medical devices and other external medical devices. IMDs may include pacemakers (also referred to as "implantable pulse generators" (IPGs) or "artificial pacemakers").

Overview

In an example, a Q-T interval adjusted for heart rate (also referred to as "Q-T corrected for heart rate" or "Q-Tc") that has a duration greater than 480 milliseconds may be considered a very high risk for ventricular tachycardia. Also, because patients implanted with pacemakers configured to pace at a lower rate limit may not become bradycardic, a sustained prolongation of the Q-T interval and heart rate flooring at the lower rate limit could lead to decreased diastolic intervals and impaired cardiac filling. These factors may increase the risk of sudden cardiac death (SCD).

Given these and other risks, health care providers may need to regularly monitor patients treated with anti-arrhythmic drugs, which may be inconvenient, costly, and/or labor intensive. Patients may need to be admitted to a hospital for multiple days for observation when initiating use of (or changing use of) a Class III anti-arrhythmic drug.

Implantable or other AMDs can include or be coupled to one or more physiologic or other sensors, such as can be configured to sense cardiac activity or one or more other characteristics such as can be associated with a patient's cardiac condition. The medical device can optionally deliver therapy such as electrical stimulation pulses to a targeted area, such as to restore or improve cardiac function. In all example, an AMD can include one or more sensors for detecting heart sounds, such as an accelerometer or microphone. Heart sounds can be associated with mechanical vibrations from activity of a patient's heart and the flow of blood through the heart. Hearts sounds recur with each cardiac cycle and can be separated and classified such as according to the activity associated with the vibration. The first heart sound (S1) is associated with the vibration sound made by the heart during tensing of the mitral valve. The second heart sound (S2) marks the beginning of diastole. The third heart sound (S3) and fourth heart sound (S4) are related to filling pressures of the left ventricle during diastole.

An EKG represents an intrinsic electrical cardiac signal, which includes atrial and ventricular depolarizations. For example, the QRS complex of the electrocardiogram can correspond to a ventricular depolarization. The time between electrocardiogram components and/or heart sounds can correspond to cardiac intervals. Cardiac intervals can correspond to cardiac activity such as diastole and systole. In an example, systole can correspond to a cardiac time interval beginning with an R-wave and ending after a T-wave. In an example, systole can correspond to a cardiac time interval beginning with a Q-wave and ending after the T-wave (also referred to as a Q-T interval). In an example, diastole can correspond to the time interval beginning with S2 and ending with S1 (also referred to as an S2-S1 interval). The Q-T interval may have a linear relationship with the Q-S2 interval, thus the Q-S2 interval can be used as a surrogate to track changes in the Q-T interval.

The present inventors have recognized, among other things, that a problem to be solved can include monitoring a patient's response to an anti-arrhythmic drug or changes in anti-arrhythmic drug use, such as using one or more sensors to acquire information about cardiac electromechanical time intervals (e.g., a cardiac time interval that can be based on an electrical fiducial component, such as from an EKG, and a mechanical fiducial component, such as a from a heart sound) or other cardiac intervals. The present subject matter can help provide a solution to this problem, such as can include using electromechanical time intervals, such as S2-R, R-S2, or other cardiac intervals, which can be adjusted for heart rate, such as to provide information about the effect of an anti-arrhythmic drug upon a patient.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document. Such embodiments are demonstrative and not intended to be exhaustive or exclusive embodiments of the present apparatuses, systems, or methods.

DETAILED DESCRIPTION

Disclosed herein are systems, devices, and methods such as can be used for monitoring an effect of an anti-arrhythmic drug upon a patient, such as can include (or consist of) using electromechanical time intervals, which can be adjusted using a heart rate of the patient. By monitoring the patient's response to the anti-arrhythmic drug such as disclosed herein, patient condition information can be detected and monitored, thereby reducing the need to follow patients using anti-arrhythmic drugs, which can be costly and labor intensive.

Figure 1:
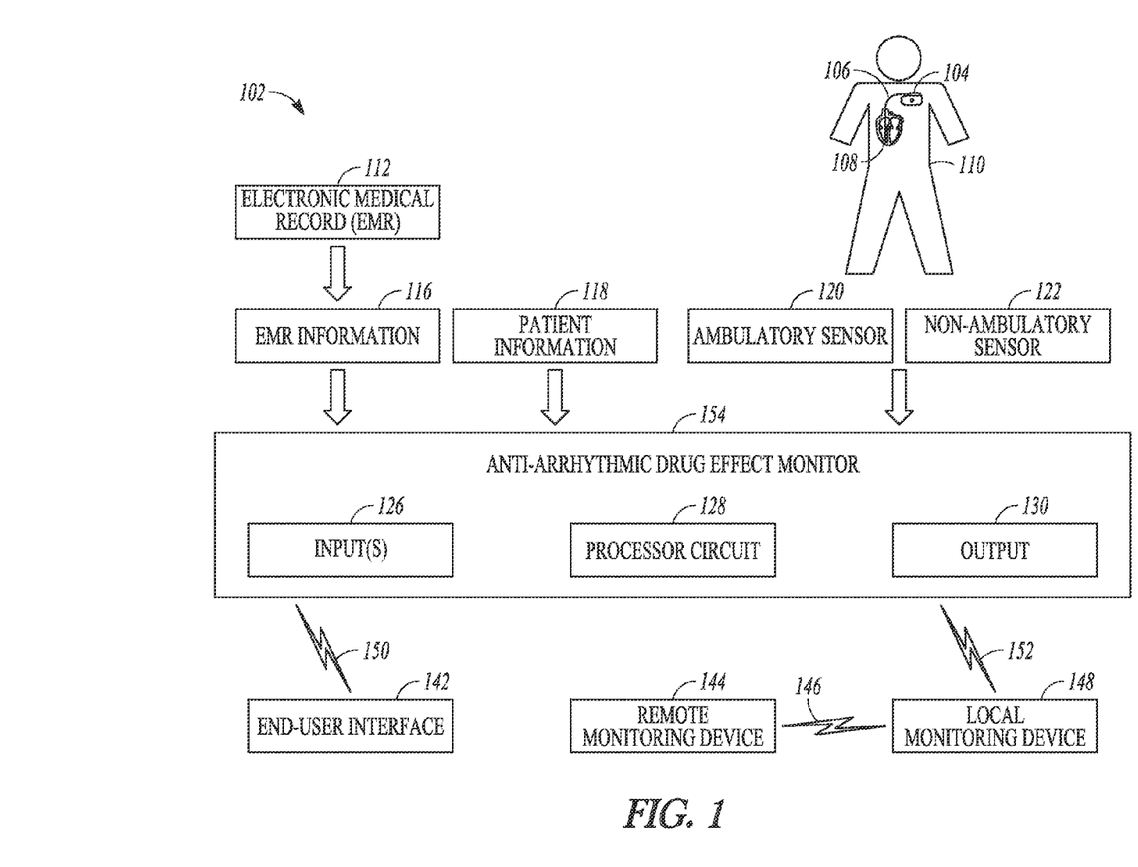
FIG. 1 illustrates an example of portions of a system to monitor an effect of an anti-arrhythmic drug upon a patient.

FIG. 1 illustrates an example of portions of a system 102 that can be used to monitor an effect of an anti-arrhythmic drug upon a patient 110. The system 102 can include an implantable medical device or other ambulatory medical device or a non-ambulatory medical device. For example, the system can include at least one of an external ambulatory sensor 120, a non-ambulatory sensor 122, or an implantable ambulatory sensor. In an example, an implantable medical device 104 can be configured to sense at least one physiological signal indicative of a physical condition of the patient 110. The implantable medical device 104 can be coupled, such as leadlessly or by one or more leads 106, to a desired location such as a heart 108. The lead 106 can include one or more electrodes (e.g. electrical contacts, such as a tip electrode, or a coil electrode, or other electrode) that can be sized, shaped, spaced, or otherwise configured to be located in or in association with the heart 108.

The system 102 can include an anti-arrhythmic drug effect monitor 154, and an end-user interface 142. The anti-arrhythmic drug effect monitor 154 can include an application-specific integrated circuit (ASIC) that can be constructed to perform one or more particular functions, or can include a hardware circuit that can be programmed to perform such one or more functions. Such a programmed hardware circuit can include a microprocessor, a microcontroller, or a programmable logic circuit, or a portion of one or more of these. In an example, the anti-arrhythmic drug effect monitor 154 can include one or more inputs 126, a processor circuit 128, and an output 130.

In an example, the anti-arrhythmic drug effect monitor 154 can be included in or associated with an implantable medical device, such as the implantable medical device 104. The implantable medical device 104 can be configured to communicate with a monitoring device or multiple monitoring devices (e.g., a local monitoring device 148 or a remote monitoring device 144) and the end-user interface 142. This communication can include using one or more communication links (e.g., communication links 146, 150, 152), such as can include a wired or wireless transmitter, receiver or transceiver circuits (such as at each end of the communication link), a communication network, or a computer network.

The anti-arrhythmic drug effect monitor 154 can be configured to determine an effect of the anti-arrhythmic drug upon the patient 110. In an example, the system 102 can include or be communicatively coupled to an electronic medical record (EMR) 112 that can include information about the patient 110, such as information about one or more physical characteristics, medical treatment or monitoring, or other patient information. Patient information 118 can include the same or different information as the EMR 112, and the patient information 118 can be stored such as using hand written or printed paper documents. Patient information 118 can additionally or alternatively be stored such as by using a computer memory (e.g., random access memories (RAMs)). Information from the EMR information 116 or the patient information 118 or both can be used by the anti-arrhythmic drug effect monitor 154 in the monitoring of an effect of the anti-arrhythmic drug upon the patient 110. In an example, the EMR information 116 and the patient information 118 can include anti-arrhythmic drug use information (e.g., administration time, drug dosage information, or the like), patient medical device use information (e.g., a pacing rate limit associated with a pacemaker, such as a lower rate limit), or other information about the patient 110.

Figure 2A:
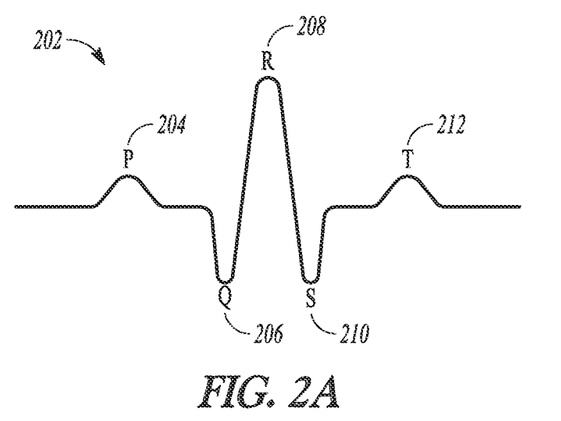
FIG. 2A is a pictorial example of an indication of a cardiac cycle.

FIG. 2A is a pictorial example of an indication of a cardiac cycle 202 of an intrinsic electrical cardiac signal. An EKG represents an intrinsic electrical cardiac signal, which includes atrial and ventricular depolarizations. The EKG can include recurring cardiac cycles that can respectively include a P-wave 204, a Q-wave 206, an R-wave 208, an S-wave 210, and a T-wave 212. FIG. 2A is illustrative of cardiac cycle components, and is not based on real human data.

Figure 2B:
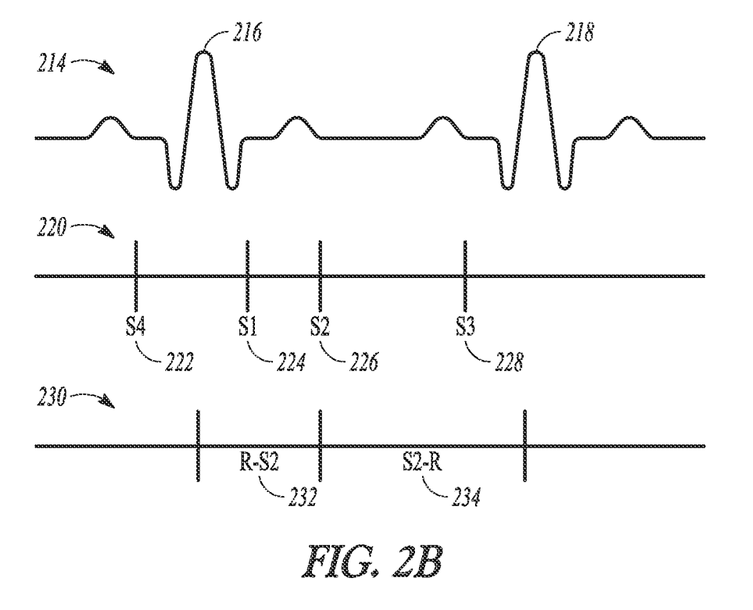
FIG. 2B is a pictorial example of cardiac interval components.

FIG. 2B is a pictorial example of cardiac interval components. An example of an intrinsic electrical heart rhythm indication 214 can include multiple cardiac cycles 202. The heart rhythm indication 214 can include a first R-wave 216 and a second R-wave 218 that can be indicative of a first and a second ventricular heart beat.

An example of a cardiac activity timeline based on mechanical activity such as heart sounds 220 can include a first heart sound (S1) 224, a second heart sound (S2) 226, a third heart sound (S3) 228, and a fourth heart sound (S4) 222. The locations in time of the heart sounds 222, 224, 226, 228 can correspond to the heart rhythm indication 214. The relative locations of components of the heart rhythm indication 214, the heart sound timeline 220, and an example of a cardiac interval timeline 230 can provide an illustrative example of relative electrical and mechanical cardiac activity. FIG. 2B is illustrative of cardiac activity, and is not based on real human data. The duration of, for example, the heart sounds 222, 224, 226, 228 and other components, are illustrative.

The example of a cardiac interval timeline 230 can include electromechanical cardiac intervals such as an R-S2 interval 232 and an S2-R interval 234. Other cardiac intervals can include electrical time intervals (e.g., Q-T, R-T, and R-R), mechanical time intervals (e.g., S1-S2 and S2-S1), time intervals based on a combination of electrical and mechanical activity of the heart (e.g., electromechanical intervals such as Q-S2 and S2-Q), or other cardiac time intervals, such as based on pressure, impedance, acoustics, other bases, or any combination thereof. The electromechanical intervals based on a combination of EKG components and heart sounds can include the R-S2 interval 232, the S2-R interval 234, or any other combination thereof.

Figure 3:
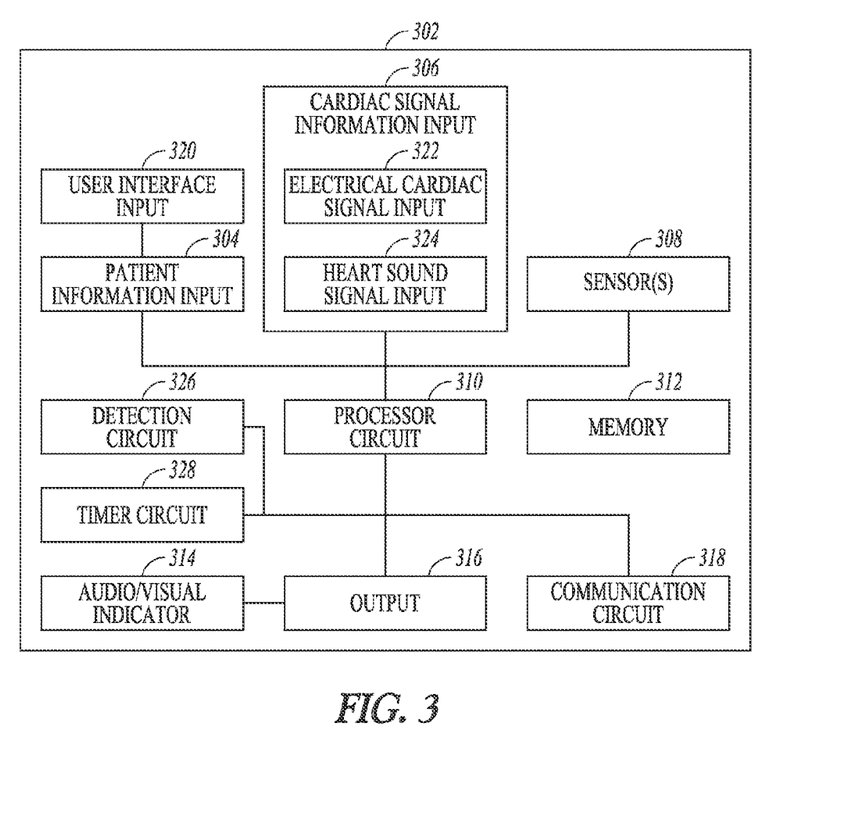
FIG. 3 illustrates an example of an anti-arrhythmic drug effect monitor configured to determine an effect of an anti-arrhythmic drug upon a patient.

FIG. 3 illustrates an example of the anti-arrhythmic drug effect monitor 154, 302 configured to determine an effect of an anti-arrhythmic drug upon a patient. The anti-arrhythmic drug effect monitor 302 can include a user interface input 320, a patient information input 304, a cardiac signal information input 306, one or more sensors 308, a detection circuit 326, a timer circuit 328, a processor circuit 310, a memory 312, an audio/visual indicator 314, an output 316, and a communication circuit 318. The processor circuit 310 can include or be coupled to the memory 312, the communication circuit 318, and a signal processor circuit that can be configured to perform digital or other signal processing or to analyze information from one or more physiological signals such as from one or more sensors 308. In an example, the processor circuit 310 can communicate with the memory 312 such as by using a data bus.

The cardiac signal information input 306 can be configured to receive information about one or more cardiac signals, and can be coupled to the processor circuit 310. In an example, the cardiac signal information input 306 can include an electrical cardiac signal input 322 and a heart sound signal input 324. The electrical cardiac signal input 322 can be configured to receive information about an electrical cardiac signal, such as can include an electrical fiducial. The heart sound signal input 324 can be configured to receive cardiac mechanical information that can include an indication such as a heart sound providing a mechanical fiducial.

The patient information input 304 can be coupled to the processor circuit 310. The patient information input 304 can be configured to receive anti-arrhythmic drug use information about the patient 110. Such anti-arrhythmic drug use information can include information such as about the anti-arrhythmic drug dosage or anti-arrhythmic drug administration time, or both. The patient information input 304 can be configured to receive anti-arrhythmic drug use information including from the EMR 112 and from the user interface input 320. In an example, the EMR 112 can be coupled, such as by a communication link, to the patient information input 304. In an example, the user interface input 320 can be coupled to the end-user interface 142 (such as can include a keyboard, a mouse, and a display) and the patient information input 304, such that an end user can enter anti-arrhythmic drug use information.

In an example, the patient information input 304 can be configured to receive information including about the detection of drug ingestion by the patient 110, where the drug can be in the form such as a pill with a radio-frequency identification tag, such as can be sensed such as by using an implantable medical device or a wearable patch.

The processor circuit 310 can include or be coupled to one or more sensors 308. As discussed above, the sensors 308 can include one or more ambulatory sensors 104, 120 or non-ambulatory sensors 122. The sensors 308 can include a heart sound sensor, an acoustic sensor (e.g., a microphone), an accelerometer (e.g., associated with the implantable medical device 104 or with the lead 106), a lead-based or other force sensor, a cardiac impedance sensor, a hemodynamic sensor (such as can be configured to monitor one or more hemodynamic parameters such as can include heart rate and blood pressure), a respiration sensor, an electrical activity sensor, a pressure sensor, a piezoelectric sensor, or one or more other sensors (such as can include external arrangements or implantable arrangements or both) such as can be configured to sense cardiac activity or one or more other characteristics such as can be associated with a patient's cardiac condition.

The detection circuit 326 can be configured to detect one or more cardiac signal components such as an R-wave 208, 316, 318 or one or more heart sounds 222, 224, 226, 228. The timer circuit 328 can be configured to determine the time between such cardiac signal components. In an example, the processor circuit 310 can be configured to determine one or more electromechanical time intervals, such as can include the R-S2 332 and S2-R 334 time intervals, such as by using information from the detection circuit 326 and the timer circuit 328. In an example, the processor circuit 310 can be configured to adjust electromechanical time intervals using a heart rate of the patient 110, such as to allow for cardiac interval analysis over time including at different heart rates.

The processor circuit 310 can be configured to determine the heart rate of the patient 110 such as by using information acquired by the sensors 308 or from inputs 126. The heart rate value used for the cardiac interval adjustment can be a heart rate value such as an "instantaneous" or "beat-to-beat" heart rate, an average or filtered reference heart rate, such as can be based on heart rates over a specified period of time, or one or more other heart rate values. The particular heart rate value used for the cardiac interval adjustment can be changed, such as based on a desired purpose.

The value of an adjusted cardiac interval can be a function of heart rate. This adjustment can include a correction, a modification, a normalization, an alteration, or any other change to the cardiac time interval based on the heart rate of the patient 110, such as by using an equation, a function, an estimated regression function, a linear regression, or one or more other relationships using the heart rate of the patient 110. In an example, the value of a Q-T interval adjusted for heart rate, Q-Tc, can be calculated such as using the R-R interval, such as by Equation 1.

$$QTc = \frac{QT}{\sqrt{RR}} \qquad \text{(Eq. 1)}$$

In Equation 1, QTc can represent a Q-T time interval adjusted for heart rate, such as can be measured in units of time (e.g., milliseconds or seconds). QT can represent a Q-T time interval (which can be indicative of cardiac systole), such as can be measured in units of time (e.g., milliseconds or seconds). RR can represent an RR time interval (which can be indicative of a heart rate), such as can be measured in units of time (e.g., milliseconds or seconds). Other cardiac intervals, such as electromechanical time intervals, can similarly be adjusted, such as by using the R-R interval or another interval corresponding to the heart rate of the patient 110.

In an example, the value of an R-S2 time interval (also referred to as "pre-ejection period" (PEP)) adjusted for heart rate, R-S2c, can be calculated such as using the R-R interval, such as by using Equation 2.

$$RS2c = \frac{PEP}{RR} \quad \text{(Eq. 2)}$$

In Equation 2, RS2c can represent a R-S2 time interval adjusted for heart rate, such as can be measured in units of time (e.g., milliseconds or seconds). PEP can represent the pre-ejection period (PEP) or an R-S2 time interval (which can be indicative of cardiac systole), such as can be measured in units of time (e.g., milliseconds or seconds). RR can represent an RR time interval (which can be indicative of a heart rate), such as can be measured in units of time (e.g., milliseconds or seconds).

In an example, the value of an R-S2 time interval adjusted for heart rate can be calculated using the R-S1 interval, such as by using Equation 3.

$$RS2c = \frac{PEP}{RS1} \quad \text{(Eq. 3)}$$

In Equation 3, RS2c can represent a R-S2 time interval adjusted for heart rate, such as can be measured in units of time (e.g., milliseconds or seconds). PEP can represent the pre-ejection period (PEP) or an R-S2 time interval (which can be indicative of cardiac systole), such as can be measured in units of time (e.g., milliseconds or seconds). RS1 can represent an R-S1 time interval, such as can be measured in units of time (e.g., milliseconds or seconds).

In an example, the value of an R-S2 time interval adjusted for heart rate can be calculated using the S1-S2 interval, such as by using Equation 4.

$$RS2c = \frac{PEP}{S1S2} \quad \text{(Eq. 4)}$$

In Equation 4, RS2c can represent a R-S2 time interval adjusted for heart rate, such as can be measured in units of time (e.g., milliseconds or seconds). PEP can represent the pre-ejection period (PEP) or an R-S2 time interval (which can be indicative of cardiac systole), such as can be measured in units of time (e.g., milliseconds or seconds). S1S2 can represent an S1-S2 time interval, such as can be measured in units of time (e.g., milliseconds or seconds).

Cardiac intervals used in monitoring the patient response to anti-arrhythmic drug changes can include heart-rate adjusted cardiac time intervals and other cardiac intervals, such as electromechanical time intervals that need not be adjusted for heart rate. In an example, the processor circuit 310 can be configured to track a change of the heart-rate adjusted electromechanical time intervals over a duration of time.

For example, the processor circuit 310 can be configured to track one or more changes in the heart-rate adjusted electromechanical time interval over one or more periods such as one or more days, weeks, or months (or any combination thereof) before or after changes to the patient's anti-arrhythmic drug use.

The processor circuit 310 can be configured to compare the duration of the heart-rate adjusted cardiac time interval to a specified time threshold. The output 316 can be configured to provide an anti-arrhythmic drug effect indication alert based on instances of the heart-rate adjusted cardiac time intervals exceeding the specified time threshold. The output 316 can be configured to provide the anti-arrhythmic drug effect indication using information about the tracked changes of the heart-rate adjusted electromechanical time intervals.

Information about the tracked changes can include the duration, such as can be measured in milliseconds, of the heart-rate adjusted electromechanical time intervals and changes in the duration over time. Generally, a patient with heart failure (also referred to as "congestive heart failure" (CHF) or "HF") can have a diastolic time interval of about 300 to about 400 milliseconds (or 300-400 milliseconds). A diastolic time interval duration that is shortened due to a pacing rate limit (e.g., a lower rate limit) can correspond to diminished atrial activity (e.g., loss of atrial kick) or passive ventricular filling. In an example, a patient with a diastolic time interval of about 250 to about 300 milliseconds (or 250-300 milliseconds) can require closer monitoring. A diastolic time interval of less than 250 milliseconds can be indicative of impaired ventricular filling. The duration of heart-rate adjusted cardiac time intervals, such as R-S2, S2-R, S2-S1, S2-S1, and other intervals (corrected for heart-rate), can be tracked to monitor the anti-arrhythmic drug effect indication, including an indication of impaired cardiac filling.

Figure 4:
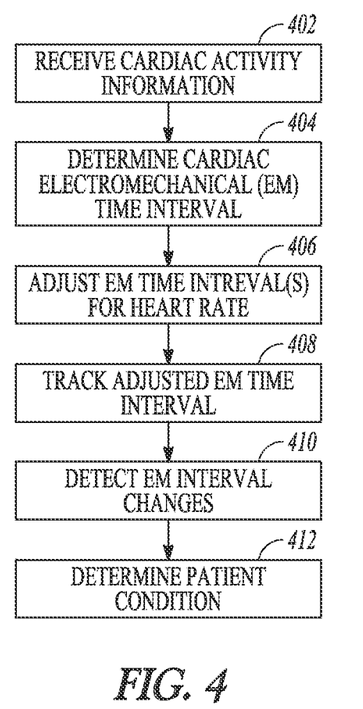
FIG. 4 illustrates an example of determining a patient's condition.

FIG. 4 illustrates an example of determining the patient's condition. At 402, cardiac activity information can be received, such as by using the cardiac signal information input 306. At 404, the cardiac electromechanical time interval can be determined, such as by using the processor circuit 310. At 406, the cardiac electromechanical time interval can be adjusted for heart rate, such as by using the processor circuit 310. At 408, the heart-rate adjusted cardiac electromechanical time interval can be tracked over time, such as by using the processor circuit 310. At 410, changes can be detected in the heart-rate adjusted cardiac electromechanical time interval, such as by using the processor circuit 310. At 412, the condition of the patient 110 can be determined based on the changes in the tracked, heart-rate adjusted cardiac electromechanical time interval, such as by using the processor circuit.

In an example, the patient condition can be determined using one or more physiological characteristics of the patient 110, such as heart rate and cardiac time interval changes. In an example, the patient condition can be determined using a combination of one or more sensors 308 and one or more physiological characteristics of the patient. In an example, the anti-arrhythmic drug effect monitor 154, 302 can be configured to determine the patient's condition based on tracked changes of one or more heart-rate adjusted cardiac electromechanical time intervals.

Figure 5:
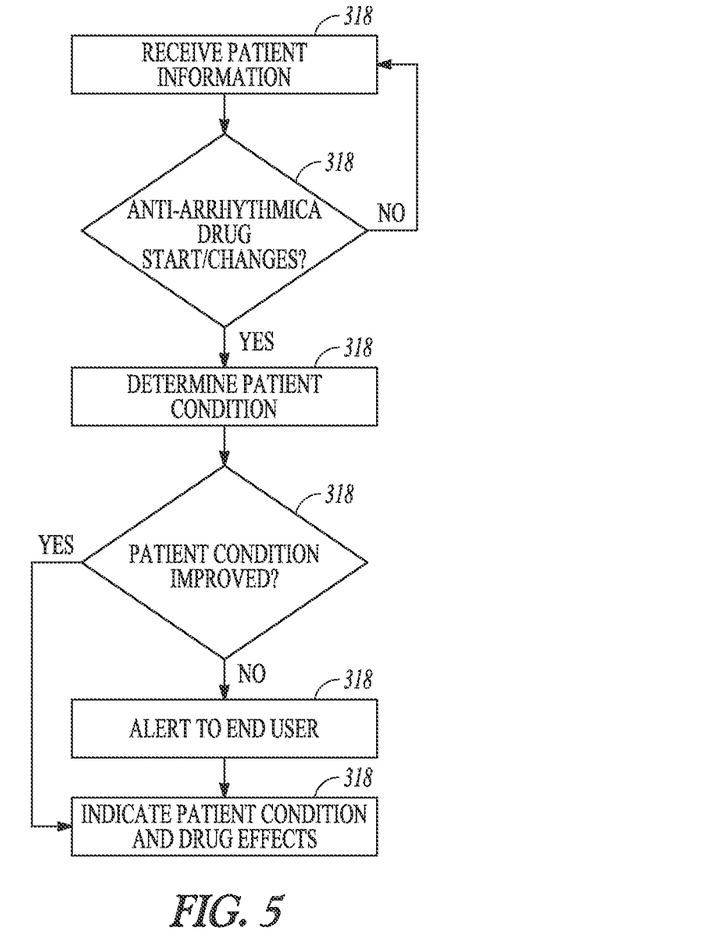
FIG. 5 illustrates an example of monitoring an effect of an anti-arrhythmic drug upon a patient.

FIG. 5 illustrates an example of monitoring an effect of an anti-arrhythmic drug upon a patient. At 502, patient information can be received, such as can include using user interface input 320, the patient information input 304, the cardiac signal information input 306, and one or more sensors 308. In an example, such patient information can include being about a start or a change in the patient's anti-arrhythmic drug use. At 504, it can be determined whether there has been a start or change in the patient's anti arrhythmic drug use, such as by using the processor circuit 310. At 506, the condition of the patient 110 can be determined, such as described above and such as using the processor circuit 310. In an example, the patient condition can be determined such as using information that can include EMR information 116 and patient information 118. At 508, it can be determined whether the condition of the patient 110 has improved, such as by using the processor circuit 310. This determination can include being based on tracked changes in one or more heart-rate adjusted electromechanical time intervals. At 510, there can be an alert to an end user, such as when the condition of the patient has not improved, and such as can include using the end-user interface 142, the output 130, 316, and the audio/visual indicator 314. At 512, the patient condition and one or more effects of the anti-arrhythmic drug upon the patient can be indicated, such as can include using the end-user interface 142, the output 130, 316, and the audio/visual indicator 314.

The anti-arrhythmic drug effect monitor 154 can be configured to provide information about the patient 110, such as including one or more effects of the anti-arrhythmic drug upon the patient 110, information about changes in the R-S2 interval over time as an indication of Q-T intervals, information about changes in the S2-R interval over time as indication of the effect of the anti-arrhythmic drug effect on cardiac filling, information about the appropriateness of drug dosage, and other information about the patient 110.

The present subject matter can be used to adjust one or more therapies such as based on information provided by the one or more of techniques described such as to decrease a risk associated with anti-arrhythmic drug use, such as sudden cardiac death. For example, the R-wave 208, 216, 218 and the heart sounds 222, 224, 226, 228 can be detected more reliably that other electromechanical time interval components (e.g., such as the Q-wave 206, which can have a smaller amplitude on the EKG than the R-wave 208, 216, 218). In an example, the present subject matter can be used in a therapy. In an example, the present subject matter can be used to treat a patient, such as can include using information from the end-user interface 142, the output 130, 316, and the audio/visual indicator 314.

Figure 6A:
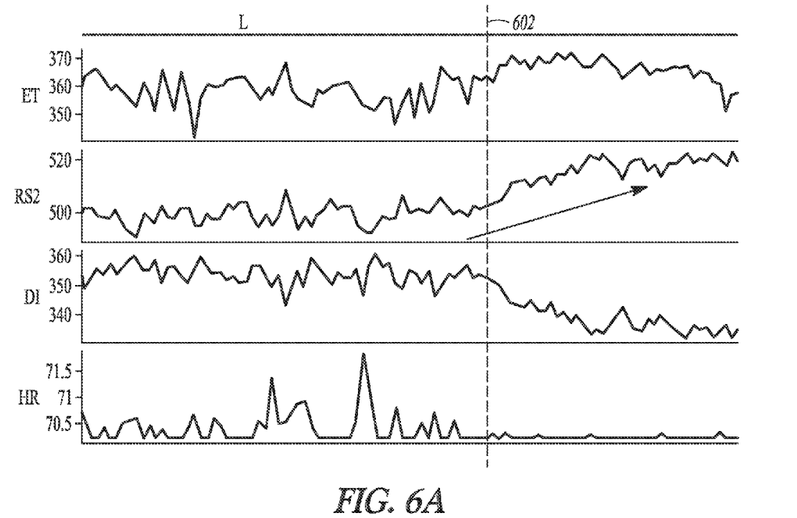
FIG. 6A illustrates an example of a graphical indication of heart-rate adjusted electromechanical intervals (and other patient information, such as including heart rate).

FIG. 6A illustrates an example of a graphical indication of heart-rate adjusted electromechanical intervals (and other patient information, such as including heart rate). FIG. 6A corresponds to clinical trial patient data. The patient of FIG. 6A started use of amiodarone at a first point in time 602. Before the first point 602, the heart rate was at a lower pacing rate limit. After the first point in time 602, the duration of the R-S2 time interval increased based on the amiodarone use, and the diastolic interval duration decreased from about 350 milliseconds to about 330 milliseconds.

Figure 6B:
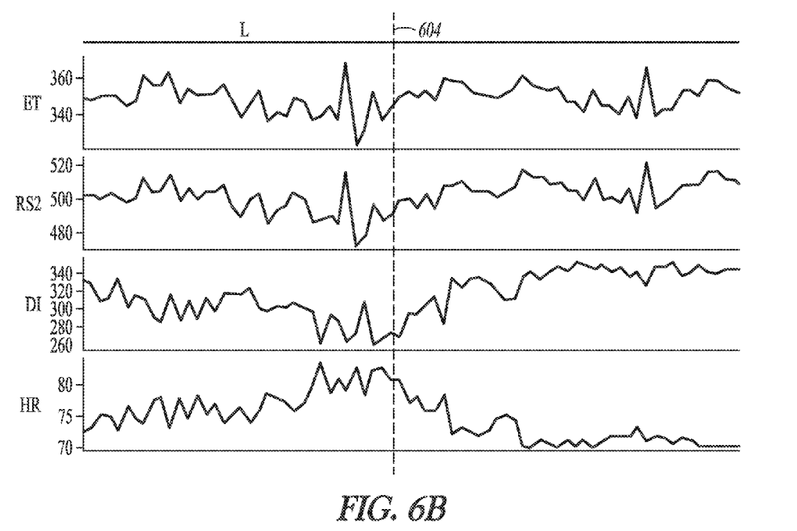
FIG. 6B illustrates an example of a graphical indication of heart-rate adjusted electromechanical intervals (and other patient information, such as including heart rate).

FIG. 6B illustrates an example of a graphical indication of heart-rate adjusted electromechanical intervals (and other patient information, such as including heart rate). FIG. 6B corresponds to clinical trial patient data. The patient of FIG. 6B started use of amiodarone at a second point in time 604. After the second point in time 604, the duration of the R-S2 time interval increased based on the amiodarone use, the heart rate decreased, and thus the diastolic interval duration increased.

In the examples of FIG. 6A and FIG. 6B, both patients, corresponding to the two graphs, were implanted with a pacemaker configured to pace at a lower rate limit.

Figure 7:
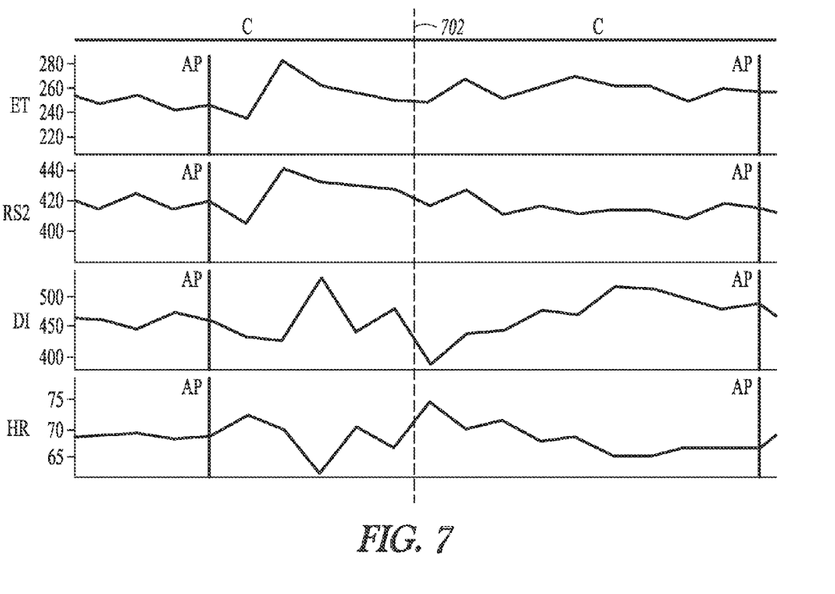
FIG. 7 illustrates an example of a graphical indication of heart-rate adjusted electromechanical intervals (and other patient information).

FIG. 7 illustrates an example of a graphical indication of heart-rate adjusted electromechanical intervals and other patient information. The patient of FIG. 7 started use of amiodarone at a third point in time 702. After the third point in time 702, the tracked intervals changed less significantly than in FIG. 6A and FIG. 6B.

In an example, monitoring a patient using an anti-arrhythmic drug using the present subject matter can decrease the cost associated with other monitoring techniques, such as regular following or admitting a patient using an anti-arrhythmic drug.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided.

Example 1 can include or use subject matter (such as a system, a method, a means for performing acts, or a machine-readable medium including instructions that, when performed by the machine, cause the machine to perform acts, etc.) that can include or use a system for monitoring an effect of an anti-arrhythmic drug upon a patient. The system can include or use an ambulatory medical device. The ambulatory medical device can include or use (1) a cardiac signal information input that can receive information about a cardiac signal and (2) a processor circuit, which can be coupled to the cardiac signal information input, that can determine a cardiac electromechanical time interval and can determine an anti-arrhythmic drug effect indication using the determined cardiac electromechanical time interval.

Some illustrative non-limiting examples of the cardiac signal information input can include, for example, an electrical cardiac signal input 322 and a heart sound signal input 324. The electrical cardiac signal input 322 can be configured to receive information about an electrical cardiac signal, such as can include an electrical fiducial. The heart sound signal input 324 can be configured to receive cardiac mechanical information that can include an indication such as a heart sound providing a mechanical fiducial.

In Example 2, the subject matter of Example 1 can optionally be configured such that the system can include or use a patient information input that can be coupled to the processor circuit. The patient information input can receive anti-arrhythmic drug use information about the patient. The processor circuit can use the anti-arrhythmic drug use information to determine the anti-arrhythmic drug effect indication.

In Example 3, the subject matter of one or any combination of Examples 1-2 can optionally be configured such that the patient information input can receive anti-arrhythmic drug use information that can include at least one of anti-arrhythmic drug dosage or anti-arrhythmic drug administration time information.

In Example 4, the subject matter of any one or any combination of Examples 1-3 can optionally be configured such that the patient information input can receive anti-arrhythmic drug use information from an electronic medical record (EMR).

In Example 5, the subject matter of one or any combination of Examples 1-4 can optionally be configured such that the patient information input can receive anti-arrhythmic drug use information from a user interface input.

In Example 6, the subject matter of one or any combination of Examples 1-5 can optionally be configured such that the processor circuit can use a pacing rate limit to determine the anti-arrhythmic drug effect indication.

In Example 7, the subject matter of one or any combination of Examples 1-6 can optionally be configured such that the cardiac signal information input can include (1) an electrical cardiac signal input that can receive information about an electrical cardiac signal including an electrical fiducial, (2) a heart sound signal input that can receive cardiac mechanical information that can include an indication of a heart sound that can provide a mechanical fiducial, and (3) the processor circuit can determine the cardiac electromechanical time interval using the electrical fiducial and the mechanical fiducial.

In Example 8, the subject matter of one or any combination of Examples 1-7 can optionally be configured such that the processor circuit can determine an electromechanical time delay using the cardiac signal.

In Example 9, the subject matter of one or any combination of Examples 1-8 can optionally be configured such that the processor circuit can determine the electromechanical time interval using (1) multiple indications of a R-S2 time interval and (2) multiple indications of a S2-R time interval.

In Example 10, the subject matter of one or any combination of Examples 1-9 can optionally be configured such that the processor circuit can adjust the electromechanical time interval using a heart rate of the patient.

In Example 11, the subject matter of one or any combination of Examples 1-10 can optionally be configured such that the processor circuit can track a change of heart-rate adjusted electromechanical time intervals.

In Example 12, the subject matter of one or any combination of Examples 1-11 can optionally be configured such that the system can include an output, which can be coupled to the processor circuit, that can provide an anti-arrhythmic drug effect indication alert based on instances of heart-rate adjusted electromechanical time intervals exceeding a specified time threshold.

In Example 13, the subject matter of one or any combination of Examples 1-12 can optionally be configured such that the output can provide the anti-arrhythmic drug effect indication alert using information about the tracked changes of the heart-rate adjusted electromechanical time intervals.

Example 14 can include or use, or can be combined with the subject matter of one or any combination of Examples 1-13 to optionally include or use, subject matter (such as an apparatus, a method, a means for performing acts, or a machine-readable medium including instruction that, when performed by the machine, cause the machine to perform acts) that can include: receiving, at an input, information about a cardiac signal; determining, at a processor circuit that can be coupled to the input, a cardiac electromechanical time interval; and determining, at the processor circuit, an anti-arrhythmic drug effect indication using the determined cardiac electromechanical time interval.

In Example 15, the subject matter of one or any combination of Examples 1-14 can optionally be configured such that the determining the anti-arrhythmic drug effect indication can include: (1) receiving, at an electrical cardiac signal input, information about an electrical cardiac signal that can include an electrical fiducial; (2) receiving, at a heart sound signal input, cardiac mechanical information that can include an indication of a heart sound that can provide a mechanical fiducial; (3) determining, using the processor circuit, the cardiac electromechanical information that can include an indication of a heart sound that can provide a mechanical fiducial; (4) adjusting, using the processor circuit, the cardiac electromechanical time interval using a heart rate of the patient; and (5) tracking, using the processor circuit, the heart-rate adjusted electromechanical time interval.

Example 16 can include or use, or can be combined with the subject matter of one or any combination of Examples 1-15 to optionally include or use, subject matter (such as an apparatus, a method, a means for performing acts, or a machine-readable medium including instructions that, when performed by the machine, cause the machine to perform acts) that can include or use a system for monitoring an effect of an anti-arrhythmic drug upon a patient. The system can include an ambulatory medical device. The ambulatory medical device can include (1) a cardiac signal information input that can receive information about a cardiac signal and (2) a processor circuit, which can be coupled to the cardiac signal information input, that can determine a cardiac electromechanical time interval and can determine an anti-arrhythmic drug effect indication using the determined cardiac electromechanical time interval.

In Example 17, the subject matter of one or any combination of Examples 1-16 can optionally be configured such that the system can include a patient information input that can be coupled to the processor circuit. The patient information input can receive anti-arrhythmic drug use information about the patient. The processor circuit can use the anti-arrhythmic drug use information to determine the anti-arrhythmic drug effect indication.

In Example 18, the subject matter of one or any combination of Examples 1-17 can optionally be configured such that the patient information input can receive anti-arrhythmic drug use information that can include at least one of anti-arrhythmic drug dosage or anti-arrhythmic drug administration time information.

In Example 19, the subject matter of one or any combination of Examples 1-18 can optionally be configured such that the patient information input can receive anti-arrhythmic drug use information from an electronic medical record (EMR).

In Example 20, the subject matter of one or any combination of Examples 1-19 can optionally be configured such that the patient information input can receive anti-arrhythmic drug use information from a user interface input.

In Example 21, the subject matter of one or any combination of Examples 1-20 can optionally be configured such that the processor circuit can use a pacing rate limit to determine the anti-arrhythmic drug effect indication.

In Example 22, the subject matter of one or any combination of Examples 1-21 can optionally be configured such that the cardiac signal information input can include (1) an electrical cardiac signal input that can receive information about an electrical cardiac signal including an electrical fiducial, (2) a heart sound signal input that can receive cardiac mechanical information that can include an indication of a heart sound that can provide a mechanical fiducial, and (3) the processor circuit can determine the cardiac electromechanical time interval using the electrical fiducial and the mechanical fiducial.

In Example 23, the subject matter of one or any combination of Examples 1-22 can optionally be configured such that the processor circuit can determine an electromechanical time delay using the cardiac signal.

In Example 24, the subject matter of one or any combination of Examples 1-23 can optionally be configured such that the processor circuit can determine the electromechanical time interval using (1) multiple indications of a R-S2 time interval and (2) multiple indications of a S2-R time interval.

In Example 25, the subject matter of one or any combination of Examples 1-24 can optionally be configured such that the processor circuit can adjust the electromechanical time interval using a heart rate of the patient.

In Example 26, the subject matter of one or any combination of Examples 1-25 can optionally be configured such that the processor circuit can track a change of heart-rate adjusted electromechanical time intervals.

In Example 27, the subject matter of one or any combination of Examples 1-26 can optionally be configured such that the system can include an output, which can be coupled to the processor circuit, that can provide an anti-arrhythmic drug effect indication based on instances of heart-rate adjusted electromechanical time intervals exceeding a specified time threshold.

In Example 28, the subject matter of one or any combination of Examples 1-27 can optionally be configured such that the output can provide the anti-arrhythmic drug effect indication alert using information about the tracked changes of the heart-rate adjusted electromechanical time intervals.

Example 29 can include or use, or can be combined with the subject matter of one or any combination of Examples 1-28 to optionally include or use, subject matter (such as an apparatus, a method, a means for performing acts, or a machine-readable medium including instructions that, when performed by the machine, cause the machine to perform acts) that can include: receiving, at an input, information about a cardiac signal; determining, at a processor circuit that can be coupled to the input, a cardiac electromechanical time interval; and determining, at the processor circuit, an anti-arrhythmic drug effect indication using the determined cardiac electromechanical time interval.

In Example 30, the subject matter of one or any combination of Examples 1-28 can optionally be configured such that the determining the anti-arrhythmic drug effect indication can include: receiving, at a patient information input that can be coupled to the processor circuit, anti-arrhythmic drug use information about the patient; and wherein the determining the anti-arrhythmic drug effect indication can include using the anti-arrhythmic drug use information about the patient.

In Example 31, the subject matter of one or any combination of Examples 1-30 can optionally be configured such that the determining the anti-arrhythmic drug effect indication can include: (1) receiving, at an electrical cardiac signal input, information about an electrical cardiac signal that can include an electrical fiducial; (2) receiving, at a heart sound signal input, cardiac mechanical information that can include an indication of a heart sound that can provide a mechanical fiducial; (3) determining, using the processor circuit, the cardiac electromechanical time interval using the electrical fiducial and the mechanical fiducial; (4) adjusting, using the processor circuit, the cardiac electromechanical time interval using a heart rate of the patient; and (5) tracking, using the processor circuit, the heart-rate adjusted electromechanical time interval.

In Example 32, the subject matter of one or any combination of Examples 1-31 can optionally be configured such as to: provide, using an output that can be coupled to the processor circuit, an anti-arrhythmic drug effect indication alert that can be based on instances of heart-rate adjusted electromechanical time intervals exceeding a specified time threshold; and provide, using the output, the anti-arrhythmic drug effect indication using information about the tracked changes of the heart-rate adjusted electromechanical time intervals.

In Example 33, the subject matter of one or any combination of Examples 1-32 can optionally be configured such that the determining the cardiac electromechanical time interval can include using; multiple indications of a R-S2 time interval; and multiple indications of a S2-R time interval.

Example 34 can include or use, or can be combined with the subject matter of one or any combination of Examples 1-33 to optionally include or use, subject matter (such as an apparatus, a method, a means for performing acts, or a machine-readable medium including instructions that, when performed by the machine, cause the machine to perform acts) that can include an apparatus to monitor an effect of an anti-arrhythmic drug upon a patient. The apparatus can include an ambulatory medical device. The ambulatory medical device can include: (1) a cardiac signal information input that can receive information about a cardiac signal; (2) a processor circuit, which can be coupled to the cardiac signal information input, that can determine a cardiac electromechanical time interval, and can determine an anti-arrhythmic drug effect indication using the determined cardiac electromechanical time interval; (3) a patient information input, that can be coupled to the processor circuit, the patient information input can receive anti-arrhythmic drug use information about the patient, and wherein the processor circuit can use the anti-arrhythmic drug use information to determine the anti-arrhythmic drug effect indication; (4) wherein the processor circuit can adjust the electromechanical time interval using a heart rate of the patient; (5) an output, which can be coupled to the processor circuit, wherein the output can provide an anti-arrhythmic drug effect indication alert based on instances of heart-rate adjusted electromechanical time intervals exceeding a specified time threshold; (6) wherein the processor circuit can track a change of heart-rate adjusted electromechanical time intervals; and (7) wherein the output can provide the anti-arrhythmic drug effect indication using information about the tracked changes of the heart-rate adjusted electromechanical time intervals.

In Example 35, the subject matter of any one or any combination of Examples 1-34 can optionally be configured such that the cardiac signal information input can include: (1) an electrical cardiac signal input that can receive information about an electrical cardiac signal including an electrical fiducial; (2) a heart sound signal input that can receive cardiac mechanical information that can include an indication of a heart sound providing a mechanical fiducial; (3) wherein the processor circuit can determine the cardiac electromechanical time interval using the electrical fiducial and the mechanical fiducial; and (4) wherein the processor circuit can adjust the electromechanical time interval using a heart rate of the patient.

Each of these non-limiting examples can stand on its own, or can be combined in various permutations or combination with one or more of the other examples.

Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for monitoring an effect of an anti-arrhythmic drug upon a patient, the system comprising:
    an ambulatory medical device comprising:
        a cardiac signal information input configured to receive information about a cardiac signal;
        a processor circuit, coupled to the cardiac signal information input, the processor circuit configured to determine a cardiac electromechanical time interval, and to determine an anti-arrhythmic drug effect indication using the determined cardiac electromechanical time interval; and
        a patient information input, coupled to the processor circuit, the patient information input configured to receive anti-arrhythmic drug use information about the patient, and wherein the processor circuit is configured to use the anti-arrhythmic drug use information to determine the anti-arrhythmic drug effect indication.

2. The system of claim 1, wherein the patient information input is configured to receive anti-arrhythmic drug use information that includes at least one of anti-arrhythmic drug dosage or anti-arrhythmic drug administration time information.

3. The system of claim 1, wherein the patient information input is configured to receive anti-arrhythmic drug use information from an electronic medical record (EMR).

4. The system of claim 1, wherein the patient information input is configured to receive anti-arrhythmic drug use information from a user interface input.

5. The system of claim 1, wherein the processor circuit is configured to use a pacing rate limit to determine the anti-antiarrhythmic drug effect indication.

6. The system of claim 1, wherein the cardiac signal information input includes:
    an electrical cardiac signal input that is configured to receive information about an electrical cardiac signal including an electrical fiducial;
    a heart sound signal input that is configured to receive cardiac mechanical information that includes an indication of a heart sound providing a mechanical fiducial; and
    wherein the processor circuit is configured to determine the cardiac electromechanical time interval using the electrical fiducial and the mechanical fiducial.

7. The system of claim 1, wherein the processor circuit is configured to determine an electromechanical time delay using the cardiac signal.

8. The system of claim 1, wherein the processor circuit is configured to determine the electromechanical time interval using:
    multiple indications of a R-S2 time interval; and
    multiple indications of a S2-R time interval.

9. The system of claim 1, wherein the processor circuit is configured to adjust the electromechanical time interval using a heart rate of the patient.

10. The system of claim 9, wherein the processor circuit is configured to track a change of heart-rate adjusted electromechanical time intervals.

11. The system of claim 10, comprising an output, coupled to the processor circuit, wherein the output is configured to provide an anti-arrhythmic drug effect indication alert based on instances of heart-rate adjusted electromechanical time intervals exceeding a specified time threshold.

12. The system of claim 11, wherein the output is configured to provide the anti-arrhythmic drug effect indication using information about the tracked changes of the heart-rate adjusted electromechanical time intervals.

13. A method for monitoring an effect of an anti-arrhythmic drug upon a patient, the method comprising:
    receiving, at an input, information about a cardiac signal;
    determining, at a processor circuit coupled to the input, a cardiac electromechanical time interval;
    determining, at the processor circuit, an anti-arrhythmic drug effect indication using the determined cardiac electromechanical time interval; and
    wherein determining the anti-arrhythmic drug effect indication includes:
        receiving, at an electrical cardiac signal input, information about an electrical cardiac signal including an electrical fiducial;
        receiving, at a heart sound signal input, cardiac mechanical information including an indication of a heart sound providing a mechanical fiducial;
        determining, using the processor circuit, the cardiac electromechanical time interval using the electrical fiducial and the mechanical fiducial;
        adjusting, using the processor circuit, the cardiac electromechanical time interval using a heart rate of the patient; and
        tracking, using the processor circuit, the heart-rate adjusted electromechanical time interval.

14. The method of claim 13, wherein the determining the anti-arrhythmic drug effect indication includes:
    receiving, at a patient information input coupled to the processor circuit, anti-arrhythmic drug use information about the patient; and
    wherein the determining the anti-arrhythmic drug effect indication includes using the anti-arrhythmic drug use information about the patient.

15. The method of claim 14, comprising:
    providing, using an output coupled to the processor circuit, an anti-arrhythmic drug effect indication alert based on instances of heart-rate adjusted electromechanical time intervals exceeding a specified time threshold; and
    providing, using the output, the anti-arrhythmic drug effect indication using information about the tracked changes of the heart-rate adjusted electromechanical time intervals.

16. The method of claim 13, wherein the determining the cardiac electromechanical time interval includes using:
    multiple indications of a R-S2 time interval; and
    multiple indications of a S2-R time interval.

17. A system for monitoring an effect of an anti-arrhythmic drug upon a patient, the system comprising:
    an ambulatory medical device comprising:
        a cardiac signal information input configured to receive information about a cardiac signal; and
        a processor circuit, coupled to the cardiac signal information input, the processor circuit configured to:
            determine a cardiac electromechanical time interval;
            determine an anti-arrhythmic drug effect indication using the determined cardiac electromechanical time interval; and
            adjust the electromechanical time interval using a heart rate of the patient.

18. The system of claim 17, comprising a patient information input, coupled to the processor circuit, the patient information input configured to receive anti-arrhythmic drug use information about the patient, and wherein the processor circuit is configured to use the anti-arrhythmic drug use information to determine the anti-arrhythmic drug effect indication.

19. The system of claim 17, wherein the cardiac signal information input includes:
    an electrical cardiac signal input that is configured to receive information about an electrical cardiac signal including an electrical fiducial;
    a heart sound signal input that is configured to receive cardiac mechanical information that includes an indication of a heart sound providing a mechanical fiducial; and
    wherein the processor circuit is configured to determine the cardiac electromechanical time interval using the electrical fiducial and the mechanical fiducial.

20. The system of claim 17, wherein the processor circuit is configured to determine the electromechanical time interval using:
    multiple indications of a R-S2 time interval; and
    multiple indications of a S2-R time interval.

* * * * *